United States Patent
Bresch et al.

(10) Patent No.: US 9,770,197 B2
(45) Date of Patent: Sep. 26, 2017

(54) DEVICE AND METHOD FOR EXTRACTING PHYSIOLOGICAL INFORMATION

(71) Applicant: KONINKLIJKE PHILIPS ELECTRONICS N.V., Eindhoven (NL)

(72) Inventors: Erik Bresch, Eindhoven (NL); Willem Verkruijsse, Veldhoven (NL); Marek Janusz Bartula, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 334 days.

(21) Appl. No.: 14/079,668

(22) Filed: Nov. 14, 2013

(65) Prior Publication Data

US 2014/0148663 A1 May 29, 2014

Related U.S. Application Data

(60) Provisional application No. 61/730,164, filed on Nov. 27, 2012.

(30) Foreign Application Priority Data

Nov. 23, 2012 (EP) ..................................... 12194032

(51) Int. Cl.
*A61B 5/1455* (2006.01)
*A61B 5/145* (2006.01)
(Continued)

(52) U.S. Cl.
CPC ........ *A61B 5/14542* (2013.01); *A61B 5/0077* (2013.01); *A61B 5/14551* (2013.01);
(Continued)

(58) Field of Classification Search
CPC ............ A61B 5/14551; A61B 5/14552; A61B 5/6826; A61B 5/6838; A61B 5/1495
See application file for complete search history.

(56) References Cited

U.S. PATENT DOCUMENTS

| 4,911,167 A | 3/1990 | Corenman et al. |
| 6,434,408 B1 | 8/2002 | Heckel |

(Continued)

FOREIGN PATENT DOCUMENTS

| JP | 2005095581 | 4/2005 | |
| NL | WO 2011042851 A1 * | 4/2011 | ......... A61B 5/02028 |
| WO | 2008/154589 | 12/2008 | |

OTHER PUBLICATIONS

Cennini, G., et al.; Heart rate monitoring via remote photoplethysmography with motion artifacts reduction; 2010; Optics Express; 18(5)4867-4875.

*Primary Examiner* — Eric Winakur

(57) ABSTRACT

The present invention relates to a device and a method for extracting physiological information from detected electromagnetic radiation emitted or reflected by a subject. A data stream derived from detected electromagnetic radiation is received. The data stream comprises a continuous or discrete characteristic signal including physiological information indicative of at least one vital parameter, the characteristic signal comprising at least one indicative signal component representative of a detected spectral portion indicative of the at least one vital parameter. The data stream at least sectionally comprises at least one auxiliary signal component detected along with the at least one indicative signal component, the at least one auxiliary signal component being representative of a distinct spectral portion. A characteristic signal discrepancy between at least one of the at least one indicative signal component and the at least one auxiliary signal component is detected, the signal discrepancy being related to a physiological state of the subject. A signal calibration parameter is determined under consideration of the detected signal discrepancy. Consequently, the at least one vital parameter can be detected under consideration of the calibration parameter.

20 Claims, 8 Drawing Sheets

(51) Int. Cl.
*A61B 5/00* (2006.01)
*A61B 5/024* (2006.01)
*A61B 5/11* (2006.01)

(52) U.S. Cl.
CPC .......... *A61B 5/7225* (2013.01); *A61B 5/7246* (2013.01); *A61B 5/02416* (2013.01); *A61B 5/1116* (2013.01); *A61B 2560/0223* (2013.01)

(56) References Cited

U.S. PATENT DOCUMENTS

| | | |
|---|---|---|
| 6,987,994 B1 | 1/2006 | Mortz |
| 7,972,266 B2 * | 7/2011 | Gobeyn ................ A61B 5/411 |
| | | 600/301 |
| 2003/0032892 A1 * | 2/2003 | Erlach ................ A61B 5/0031 |
| | | 600/547 |
| 2003/0144584 A1 | 7/2003 | Mendelson |
| 2004/0220460 A1 | 11/2004 | Roberts |
| 2005/0222502 A1 | 10/2005 | Cooper |
| 2008/0208019 A1 | 8/2008 | Nitzan |
| 2008/0208020 A1 | 8/2008 | Cinbis et al. |
| 2008/0292151 A1 * | 11/2008 | Kurtz ..................... A61B 3/10 |
| | | 382/128 |
| 2009/0245591 A1 * | 10/2009 | Rowe .................. G06K 9/2018 |
| | | 382/115 |
| 2010/0014723 A1 * | 1/2010 | Addison ........... A61B 5/14551 |
| | | 382/128 |
| 2010/0298651 A1 | 11/2010 | Moon et al. |
| 2010/0298655 A1 * | 11/2010 | McCombie .......... A61B 5/0002 |
| | | 600/301 |
| 2012/0108915 A1 * | 5/2012 | Corbucci ........... A61B 5/02028 |
| | | 600/301 |
| 2012/0253156 A1 | 10/2012 | Muhlsteff |
| 2013/0345568 A1 * | 12/2013 | Mestha ............. A61B 5/02405 |
| | | 600/479 |
| 2014/0031696 A1 | 1/2014 | Schmeitz |
| 2014/0303454 A1 * | 10/2014 | Clifton ................ A61B 5/0205 |
| | | 600/479 |

* cited by examiner

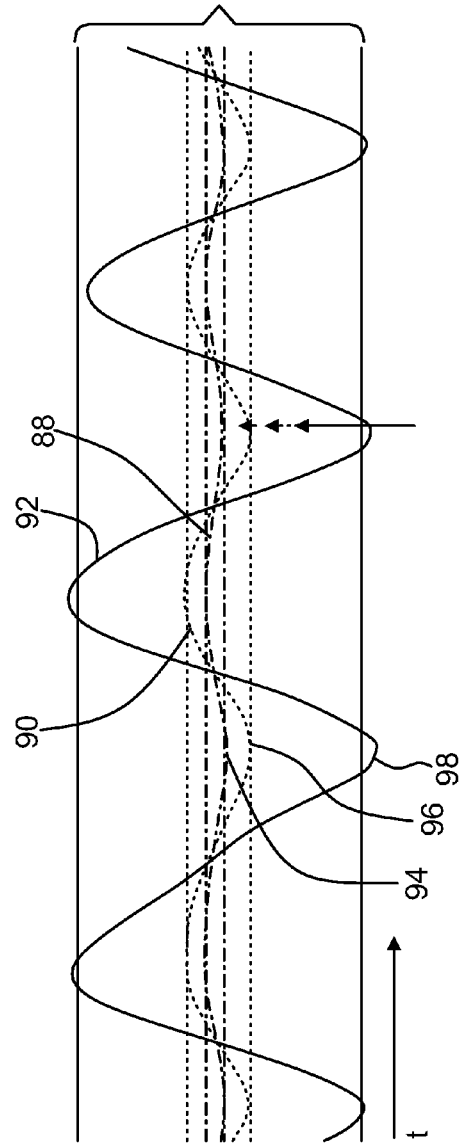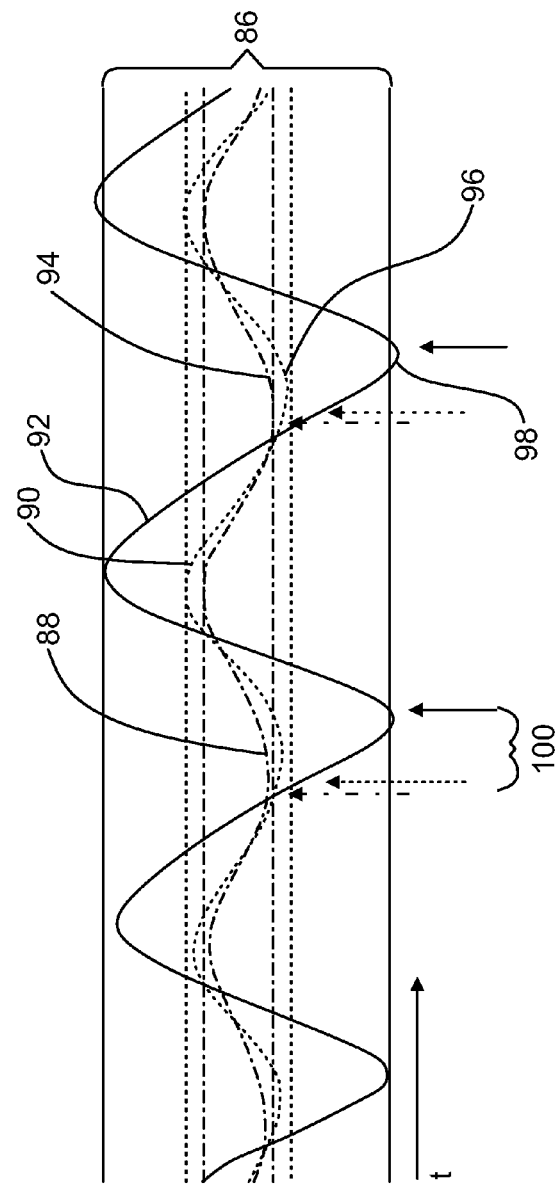

DEVICE AND METHOD FOR EXTRACTING PHYSIOLOGICAL INFORMATION

CROSS REFERENCE TO RELATED APPLICATIONS

This application claims the benefit of EP provisional application serial no. 12194032.4 filed Nov. 23, 2012 and U.S. provisional application Ser. No. 61/730,164 filed Nov. 27, 2012, both of which are incorporated herein by reference.

FIELD OF THE INVENTION

The present disclosure relates to a device and a method for extracting physiological information from detected electromagnetic radiation emitted or reflected by a subject. In particular, the present disclosure relates to unobtrusive optical measurement approaches which can be used for detecting physiological parameters in an observed subject. In this connection, optical measurement may refer to photoplethysmography (PPG) and, more specifically, to pulse oximetry. More particularly, but likewise non-restricting, the present disclosure may further relate to remote photoplethysmography approaches. The present disclosure further relates to a computer readable non-transitory medium.

BACKGROUND OF THE INVENTION

U.S. Pat. No. 6,434,408 B1 discloses a system and a method related to improvements in pulse oximetry approaches. In particular, a method for use in a pulse oximetry system which provides a detector output indicative of light absorption by a tissue-under-test at each of a plurality of different light wavelengths is presented, the method comprising:

utilizing said detector output to compute blood analyte indicator values for each of a plurality of measurements, and obtaining a corresponding relative motion estimate value for each of said plurality of measurements; and, determining whether the corresponding relative motion estimate value for each of said plurality of measurements is within a first predetermined range, wherein for at least one of said plurality of measurements having a corresponding relative motion estimate value within a first predetermined range the corresponding blood analyte indicator value is adjusted utilizing a predetermined adjustment factor that is empirically determined, and wherein said adjusted blood analyte indicator value is employable to obtain a blood analyte concentration value.

The document further discloses several refinements of the method and the system. The document is particularly directed to patient monitoring, such as monitoring a patient's blood oxygen saturation ($SpO_2$). In this connection, pulse oximetry making use of photoplethysmographic approaches can be utilized. For instance, light signals corresponding to two or more different wavelength portions can be employed to non-invasively determine blood components. Basically, blood oxygen saturation measurement can be based on measuring the absorption of oxyhemoglobin (oxygenated hemoglobin) and so-called reduced hemoglobin. Differences in the respective absorption behavior can be indicative of a present $SpO_2$ level. In this connection, it can be exploited that the reduced hemoglobin typically absorbs more light than oxyhemoglobin in a first wavelength portion and, vice versa, that oxyhemoglobin absorbs more light than reduced hemoglobin in a second distinct wavelength portion.

Basically, photoplethysmography is considered a conventional technique which can be used to detect blood volume changes in the tissue of a monitored subject. Conventionally known PPG-approaches include so-called contact PPG devices which can be attached to the skin of the subject of interest, for instance to a finger tip or earlobe. The PPG waveform typically comprises a pulsatile physiological waveform attributable to cardiac synchronous changes in the blood volume with every heart beat. Besides that, the PPG waveform can comprise further embedded information attributable to respiration, oxygen saturation, and to even further physiological phenomena.

Although even standard PPG is considered a basically non-invasive technique, contact PPG requires measurement components (e.g., light sources and photo detectors) which basically have to be attached to the subject's skin. Consequently, standard photoplethysmography still comprises somewhat obtrusive measurements, e.g. via a transceiver unit being firmly fixed to the subject's earlobe or finger tip. Therefore, contact PPG measurement is often experienced as being unpleasant.

Typically, a standard (or: contact) PPG device includes artificial light sources to be directly attached to an indicative surface, e.g., a skin portion, of the subject to be observed. In this manner, reduction or even avoidance of adverse effects is achieved. For instance, potentially disturbing incident radiation caused by other (or: ambient) light sources and undesired subject motion with respect to the light sources can be addressed in this way. Correspondingly, in contact PPG devices also the receiver or detector, e.g. at least one photodiode, is closely fixed to the subject's skin patch of interest. In case the transceiver unit is too firmly fixed to the subject so as to avoid subject movement with respect to the equipment, signal quality can be deteriorated as well, e.g. due to undesired tissue compression.

Recently, remote PPG approaches applying unobtrusive measurements have been introduced. Basically, remote photoplethysmography utilizes light sources or, in general radiation sources, disposed remote from the subject of interest, preferably, for some applications even readily available existing (ambient) light sources rather than defined special-purpose light sources are utilized. For instance, artificial light sources and/or natural light sources can be exploited. Consequently, in remote PPG environments, it has to be expected that due to widely changing illumination conditions, the detected signals generally provide a very small signal-to-noise ratio. Similarly, also a detector, e.g., a camera or at least one photodetector, can be disposed remote from the subject of interest for remote PPG measurements. Therefore, remote photoplethysmographic systems and devices are considered unobtrusive and can be adapted and well suited for everyday application. The field of application may comprise unobtrusive in-patient and out-patient monitoring and even leisure and fitness applications. In this regard, it is considered beneficial that observed subjects can enjoy a certain degree of freedom of movement during remote PPG measurement.

Consequently, compared with standard (obtrusive) photoplethysmography, remote (unobtrusive) photoplethysmography is far more susceptible to distortion and noise. Undesired subject motion with respect to the detector and/or the radiation source can excessively influence signal detection.

In summary, remote PPG is still considered to pose major challenges to signal detection and signal processing. Since the recorded data, such as captured, reflected or emitted electromagnetic radiation (e.g. recorded image frames) always comprises, besides the desired signal to be extracted therefrom, further signal components deriving from overall disturbances, for instance noise due to changing luminance conditions and/or relative motion between the observed subject and the detection sensor, a detailed precise extraction of the desired signals is still considered to pose major problems for existing detection approaches and processing algorithms.

An important field for PPG measurements is the determination of blood oxygen saturation. Contact pulse oximeters typically transmit red and infrared (or, more precisely, in some cases near infrared) light through a vascular tissue of the subject of interest. The respective light portions (R/IR) can be transmitted and detected in an alternating (fast-switching) manner. Given that the respective spectral portions are differently absorbed by oxygenated hemoglobin ($HbO_2$) and reduced hemoglobin (Hb), blood oxygen saturation eventually can be processed. An oxygen saturation ($SpO_2$) estimation algorithm can make use of a ratio of the signals related to the red and the infrared portion. Furthermore, the algorithm can consider a non-pulsatile signal component. Typically, the PPG signal comprises a DC component and a relatively small pulsatile AC component. Furthermore, $SpO_2$ estimation generally involves an empirically derived calibration factor applied to the processed values. Typically, the calibration factor (or, calibration curve) is determined upon reference measurements involving invasive blood oxygen saturation measurements. A calibration factor is required since a PPG device basically detects a ratio of (spectral) signal portions which has to be transferred into a blood oxygen saturation value which typically involves a ratio of $HbO_2$ and Hb. For instance, but not intended to limit the present disclosure, blood oxygen saturation estimation can be based on the following general equation:

$$S_pO_2 = \frac{(HbO)_2}{HbO_2 + H_b}, \quad (1)$$

whereas PPG devices merely mediately detect $HbO_2$ and Hb.

SUMMARY OF THE INVENTION

It is therefore an object of the present invention to provide a system and a method for extracting physiological information from detected electromagnetic radiation emitted or reflected by a subject providing further refinements facilitating obtaining and processing the desired signals with higher accuracy. It would be further advantageous to provide a device and a method even more adapted for enabling signal detection and extraction in remote PPG environments which may involve further disturbing influences. It would be yet even further advantageous to provide a method and a device allowing for unobtrusive monitoring and vital signal detection at an accuracy level which may satisfy health care requirements.

In a first aspect of the present disclosure a device for extracting physiological information from detected electromagnetic radiation emitted or reflected by a subject, comprising:

an interface that receives a data stream derived from detected electromagnetic radiation, the data stream comprising a continuous or discrete characteristic signal including physiological information indicative of at least one vital parameter, the characteristic signal comprising at least one indicative signal component representative of a detected spectral portion indicative of the at least one vital parameter, the data stream at least sectionally comprising at least one auxiliary signal component detected along with the at least one indicative signal component, the at least one auxiliary signal component being representative of a distinct spectral portion, a signal comparator that detects a characteristic signal discrepancy between at least one of the at least one indicative signal component and the at least one auxiliary signal component, the signal discrepancy being related to a physiological state of the subject, and a calibration processor that determines a signal calibration parameter under consideration of the detected signal discrepancy.

The present disclosure is based on the insight that for vital signal monitoring applications even further disturbances may occur which may even have no relevance or only minor relevance for commonly known contact monitoring approaches. As indicated above, directly attaching transceiving units to the subject's tissue may eliminate or, at least, reduce several disturbing influences. For instance, contact PPG monitoring typically provides for a fixed and steady relative position of the monitoring device and the subject's tissue to be monitored. By contrast, remote monitoring typically allows for a certain freedom of motion between the subject of interest and the respective components of the device. In this connection, it has been realized that, in some remote monitoring environments, applying a "fixed" calibration parameter to the detected signals is often insufficient since in this way no account is taken of typical disturbances arising from the actual monitoring configuration which may involve various distances for radiation rays when being transmitted from the illumination source to the subject of interest and, eventually, to the sensing device. Furthermore, standard contact vital signal monitoring devices typically make use of predefined transceiver units such as, for instance, illumination sources and respective sensor elements adapted to predefined monochrome or, at least, quasi-monochrome wavelength portions. According to some embodiments, when applying broadband illumination devices or even broadband wide filed illumination devices, broadband illumination may influence the monitoring performance. Also in this connection, the "fixed" calibration parameter approach may be considered rather disadvantageous.

According to the present disclosure the calibration parameter can be considered an adjustable calibration parameter. Calibration parameter adjustment is performed under consideration of the detected signal discrepancy. It has been realized that disturbances related to certain monitoring peculiarities typically have different effects on different spectral portions of the detected signals. This may apply to remote monitoring approaches, for example. Therefore, given that the device is configured for detecting the signal discrepancy arising from these different effects, the calibration parameter can be adjusted accordingly and, eventually, the processed signals can be compensated for remote monitoring related disturbances, at least to a certain extent.

It should be understood that the at least one indicative signal component and the at least one auxiliary signal component can be detected by observing and monitoring the same or, at least, basically the same region of interest in the subject. For instance, the region of interest of the subject can be formed by a forehead portion of the subject. In general, a skin portion of the subject can form the region of interest from which the at least one indicative signal component and the at least one auxiliary signal component can be extracted.

It should be further noted that the at least one indicative signal component and the at least one auxiliary signal component can be recorded in parallel or in an alternating sequence. Given that the data stream can be composed of frames captured at a defined frame rate, alternatingly succeeding frames can be representative of the at least one indicative signal component or the at least one auxiliary signal component. However, in the alternative, the data stream can be composed of at least two sequences of frames each of which exclusively representing either the at least one auxiliary signal component or the at least one indicative signal component. In one embodiment, the data stream comprises three sequences of frames. A first sequence represents a first indicative signal component representative of a first spectral portion. A second sequence represents a second indicative signal component representative of a second spectral portion. A third sequence represents a first auxiliary signal component representative of a third spectral portion. In still yet another alternative, the data stream may comprise a single sequence of signal samples (or: frames) each of which indicative of a broad spectral portion such that both the at least one indicative signal component and the at least one auxiliary component can be derived therefrom.

As used herein, the term "radiation emitted or reflected by a subject" may generally refer to radiation which is emitted towards and eventually re-emitted by the subject of interest. For instance, incident radiation may be specularly reflected at the subject's skin surface. Furthermore, incident radiation may be diffusely reflected at subjacent portions of the subject's skin tissue. Still, however, incident radiation may also be transmitted through the subject's skin tissue, for instance at the fingertip or the earlobe. Transmission of radiation may involve direct transmission, but also deflected transmission. All these events may be covered by the term "re-emitted". Typically, re-emitted radiation can be composed of several portions which may have been subjected to various types of reflection or transmission.

As indicated above, the data stream can comprise a sequence or a set of sequences of frames or, more precisely, a series or a set of series of image frames comprising spectral information based on a representation of the region of interest.

According to another aspect, it can be envisaged that the at least one auxiliary signal component is merely temporarily present in the data stream. In some embodiment, the at least one auxiliary signal component is present all along in the data stream but, rather, merely temporarily processed. Since the at least one auxiliary signal component serves as a "reference" for detecting the signal discrepancy which, given that the subject is not constantly changing posture, can be considered a parameter showing little dynamic changes, it may be sufficient in many cases that the signal discrepancy value is updated from time to time. Still, however, according to some alternative aspects, it can be envisaged that the signal discrepancy is constantly updated which basically requires that the auxiliary signal component is constantly present and processed accordingly.

There exist several embodiments of the signal comparator and the calibration processor. In a first, fairly simple embodiment, the signal comparator and the calibration processor are commonly embodied by a processor unit which is driven (or: controlled) by respective logic commands. Such a processing unit may also comprise suitable input and output interfaces. The processing unit can comprise further processing means, for instance a signal analyzing unit.

However, in the alternative, each of the signal comparator, the calibration processor and, if any, an analyzing unit and further processing means can be embodied by separate processing units, controlled or controllable by respective commands. Hence, each respective processing unit can be adapted to its special purpose. Consequently, a distribution of tasks can be applied, wherein distinct tasks are processed (or: executed) on a single processor of a multi-processor processing unit, or wherein image processing related tasks are executed on an image processor while other operational tasks are executed on a central processing unit.

As used herein, the physiological state of the subject which is indicated by the signal discrepancy may relate to a physical state of the subject, such as the subject's actual posture (e.g., sitting, lying, standing upright, or being in an upside down posture). The physiological state may further relate to an actual acceleration the subject experiences. In this connection, changes in gravitational acceleration, reduced or increased gravitation environments, or even zero-gravitation environments may be addressed, for example. This may apply, for instance, to astronauts or pilots, to athletes or race drivers, but also to theme park visitors (e.g., when riding a rollercoaster) and to further subjects. Furthermore, a current physiological state condition of the subject may relate to hypertension, excitement, or even to further stressful situations the subject experiences. In this connection, more generally, the physiological state may also relate to abnormal conditions of the subject's circulatory system.

According to another aspect of the present disclosure, the device further comprises an analyzing unit for detecting the at least one vital parameter under consideration of the calibration parameter. Since the calibration parameter is an adaptive or adjustable calibration parameter, the at least one vital parameter can be derived with higher accuracy allowing to account for remote monitoring related fault effects.

According to another aspect, the signal discrepancy is a temporal signal discrepancy representative of an actual posture of the subject. This aspect is based on the insight that, for remote monitoring environments, a change of the subject's posture indeed can be reflected in the detected vital parameters, provided that a "fixed" calibration parameter is utilized.

According to yet another aspect the signal discrepancy is a temporal signal discrepancy representing a time delay between the at least one of the at least one indicative signal component and the at least one auxiliary signal component.

A posture change of the subject can be reflected in the detected signals in that characteristic signal portions in one signal component are lagging behind corresponding characteristic signal portions in another signal component. Basically, the at least one auxiliary signal component can be chosen such that a considerable time delay or lag occurs when the subject's posture is changed. For instance, at an initial posture (e.g., the subject is sitting) only a small or even no time delay between the at least one of the at least one indicative signal component and the at least one auxiliary signal component is detectable. By contrast, in a second posture (e.g., the subject is lying) a considerable large time delay or gap between the at least one of the at least one indicative signal component and the at least one auxiliary component is detectable. Based on a detected time delay value, the calibration parameter can be adjusted. For detecting the time delay characteristic signal portions can be tracked and compared. The characteristic signal portions can be formed by signal minima, signal maxima, extreme values in general, saddle points, inflection points, etc.

According to yet another aspect the signal discrepancy is a signal form discrepancy representing differences in waveform, in particular differences in amplitude, between the at least one of the at least one indicative signal component and the at least one auxiliary signal component. Also in this way a signal discrepancy can be detected which can be utilized for adjusting the calibration parameter so as to improve the vital parameter detection's accuracy. Also signal discrepancies reflected in differences in signal waveform can be related to and indicative of posture changes of the subject with respect to the monitoring device.

According to even yet another aspect the at least one vital parameter is a parameter derivable from cardiovascular activity, wherein the parameter is preferably chosen from the group consisting of oxygen saturation, heart beat, heart rate, heart rate variability, Traube Hering Mayer waves, and respiration rate.

Preferably, the device of the disclosure is utilized for oxygen saturation ($SpO_2$) measurements. As indicated above, blood oxygen saturation is mediately derived from PPG signals. Hence, when adopting remote PPG approaches to this field of application, further disturbing influences have to be considered. This influences can be considered unique in that they are not present in contact blood oxygen saturation measurements and, furthermore, of no or, at least, of minor relevance for remote PPG monitoring approaches primarily addressing vital parameters which are "directly" linked to the detected cardiovascular activity signals, such as heart rate signals.

According to another aspect, the calibration parameter is an adaptive calibration parameter, wherein the calibration processor is configured for computing the calibration parameter under consideration of statistical adjustment computation measures applying the detected signal discrepancy.

In this connection it is envisaged to conduct preparatory reference measurements so as to determine a correlation link between the detected signal discrepancy and a corresponding adjustment of the calibration parameter. The correlation link can involve a correlation equation. The correlation link can be stored in the calibration processor. The signal discrepancy, for instance, the detected time delay, can serve as an input value upon which a resulting adjustment value can be calculated. Based on a set of reference measurement values regression analyses can be applied so as to detect the relationship between the detected signal discrepancy and a required calibration parameter adjustment. This may contribute in ensuring that a vital parameter of interest eventually can be detected at a desired accuracy. Regression analyses may result in a regression line or, more generally, in a regression curve. The regression line or curve can be described or characterized by a respective calibration equation.

According to another aspect it is further preferred that the signal comparator is configured for detecting the signal discrepancy by applying a correlation computation to the at least one of the at least one indicative signal component and the at least one auxiliary signal component. Such a comparative computation may involve cross-correlation measures, phase-correlation measures and/or feature correlation measures in general. Signal correlation can be directed to characteristic signal portions in the at least one of the at least one indicative signal component and the at least one auxiliary signal component. As indicated above, the characteristic signal components can comprise minima, maxima, extreme values in general, etc.

According to yet another aspect, the characteristic signal comprises at least two indicative signal components, wherein a first signal component is representative of a first indicative spectral portion, in particular a visible-light portion, and wherein a second signal component is representative of a second indicative spectral portion, in particular an infrared portion. As indicated above, applying red light and infrared (or: near infrared) light to the subject and monitoring respective light transmission or reflection may result in indicative signal components based on which blood oxygen saturation can be computed.

It is further preferred in this connection that the at least one auxiliary signal component is representative of an auxiliary spectral portion, wherein the auxiliary spectral portion and at least one of the first indicative spectral portion and the second indicative spectral portion are chosen such that different respective absorption and reflection characteristics appear in an observed tissue of the subject.

Basically, radiation absorbance and, consequently, radiation reflectance and radiation transmittance in blood (or, more precisely, in hemoglobin) is dependent on the wavelength of incident radiation. Moreover, absorbance, transmittance and reflectance of radiation in blood vessels and surrounding tissue differ significantly from one another.

It is preferred that the respective spectral portions of the at least one auxiliary signal component and at least one of the indicative signal components are significantly spaced in the wavelength band. This idea can make use of the fact that a penetration depth of radiation which is dependent on blood absorption and tissue absorption is basically also dependent on the wavelength of incident radiation. Typically, infrared (or: near infrared) and red light penetrates deeper into the subject's tissue than visible light having shorter wavelengths. By way of example, the auxiliary spectral portion can be formed of a band or sub-band in the green portion of visible radiation.

According to yet another aspect, the device further comprises a sensor unit, in particular a camera, configured for capturing electromagnetic radiation at a distance, wherein the sensor unit comprises a defined response characteristic adapted to at least two defined spectral distributions.

It is emphasized that the sensor unit is particularly suited for remote monitoring applications. The sensor unit can comprise one or more sensing elements. For instance, the sensor unit can comprise an array of photodiodes or charge-coupled devices. According to another aspect, the sensor unit comprises at least two groups of sensor elements each of which is configured for detecting a single one of the at least one indicative signal component and the at least one auxiliary signal component. According to yet another aspect, the sensor unit can make use of a single group of sensor elements having a response characteristic allowing for a detection of each of the at least one indicative signal component and the at least one auxiliary signal component. A device having such a sensor unit can be further configured for capturing a sequence which is composed of an alternating series of frames alternatingly representing the at least one indicative signal component and the at least one auxiliary component.

It is even further preferred that the device comprises at least one source of electromagnetic radiation configured for directing radiation to the subject at a distance, in particular a source capable of generating radiation portions comprising visible radiation and infrared radiation. The at least one source of radiation can be embodied by a broadband illumination source. The at least one source of radiation can make use of a single group or two or even more groups of radiation elements.

The device of the disclosure does not necessarily have to comprise a source of electromagnetic radiation. The device can also make use of ambient light sources which are not connected to the device.

The at least one source of electromagnetic radiation can be synchronized with the sensor unit. An emittance frequency of the at least one source of electromagnetic radiation can be adapted to a frame rate of the sensor unit. The at least one source of electromagnetic radiation can be configured for emitting an alternating recurring series of radiation portions respectively representative, for example, of the first indicative spectral portion, the second indicative spectral portion, and the auxiliary spectral portion.

In a further aspect of the present disclosure, a method for extracting physiological information from detected electromagnetic radiation emitted or reflected by a subject is presented, the method comprising the steps of:

receiving a data stream derived from detected electromagnetic radiation, the data stream comprising a continuous or discrete characteristic signal including physiological information indicative of at least one vital parameter, the characteristic signal comprising at least one indicative signal component representative of a detected spectral portion indicative of the at least one vital parameter, the data stream at least sectionally comprising at least one auxiliary signal component detected along with the at least one indicative signal component, the at least one auxiliary signal component being representative of a distinct spectral portion, detecting a characteristic signal discrepancy between at least one of the at least one indicative signal component and the at least one auxiliary signal component, the signal discrepancy being related to a physiological state of the subject, and determining a signal calibration parameter under consideration of the detected signal discrepancy.

Advantageously, the method can be carried out utilizing the device for extracting physiological information of the disclosure.

According to another aspect, the method further comprises the steps of:

computing the calibration parameter under consideration of statistical adjustment computation measures applying the detected signal discrepancy, and detecting the at least one vital parameter under consideration of the calibration parameter.

In yet another aspect of the present disclosure, there is provided a computer readable non-transitory medium having instructions stored thereon which, when carried out on a computer, cause the computer to perform the steps of a method in accordance with the present disclosure. The program code (or: logic) can be encoded in one or more non-transitory, tangible media for execution by a computing machine, such as a computer. In some exemplary embodiments, the program code may be downloaded over a network to a persistent storage from another device or data processing system through computer readable signal media for use within the device. For instance, program code stored in a computer readable storage medium in a server data processing system may be downloaded over a network from the server to the device. The data processing device providing program code may be a server computer, a client computer, or some other device capable of storing and transmitting program code.

As used herein, the term "computer" stands for a large variety of processing devices. In other words, also mobile devices having a considerable computing capacity can be referred to as computing device, even though they provide less processing power resources than standard desktop computers. Furthermore, the term "a computer" may also refer to a distributed computing device which may involve or make use of computing capacity provided in a cloud environment.

Preferred embodiments of the invention are defined in the dependent claims. It should be understood that the claimed method and the claimed computer program can have similar preferred embodiments as the claimed device and as defined in the dependent device claims.

BRIEF DESCRIPTION OF THE DRAWINGS

These and other aspects of the invention will be apparent from and elucidated with reference to the embodiments described hereinafter. In the following drawings

FIG. 2a exemplarily illustrates a sequence representing a subject of interest which is monitored in different posture situations;

FIG. 2b shows a diagram representing a reference measurement applied to a subject in an environment illustrated in FIG. 2a;

FIG. 2c illustrates a remote measurement simultaneously applied to a subject in the environment illustrated in FIG. 2a;

FIGS. 7a, 7b show exemplary diagrams illustrating signal curves representing indicative signal components and an auxiliary signal component, wherein the diagrams represent different subject postures;

DETAILED DESCRIPTION OF THE INVENTION

The following section describes exemplary approaches to photoplethysmography, in particular to remote blood oxygen saturation measurement, utilizing several aspects of the device and method in accordance with the present disclosure. It should be understood that single steps and features of the shown approaches can be extracted from the context of the respective overall approach or embodiment. These steps and features can therefore be part of separate embodiments still covered by the scope of the invention.

Figure 1:
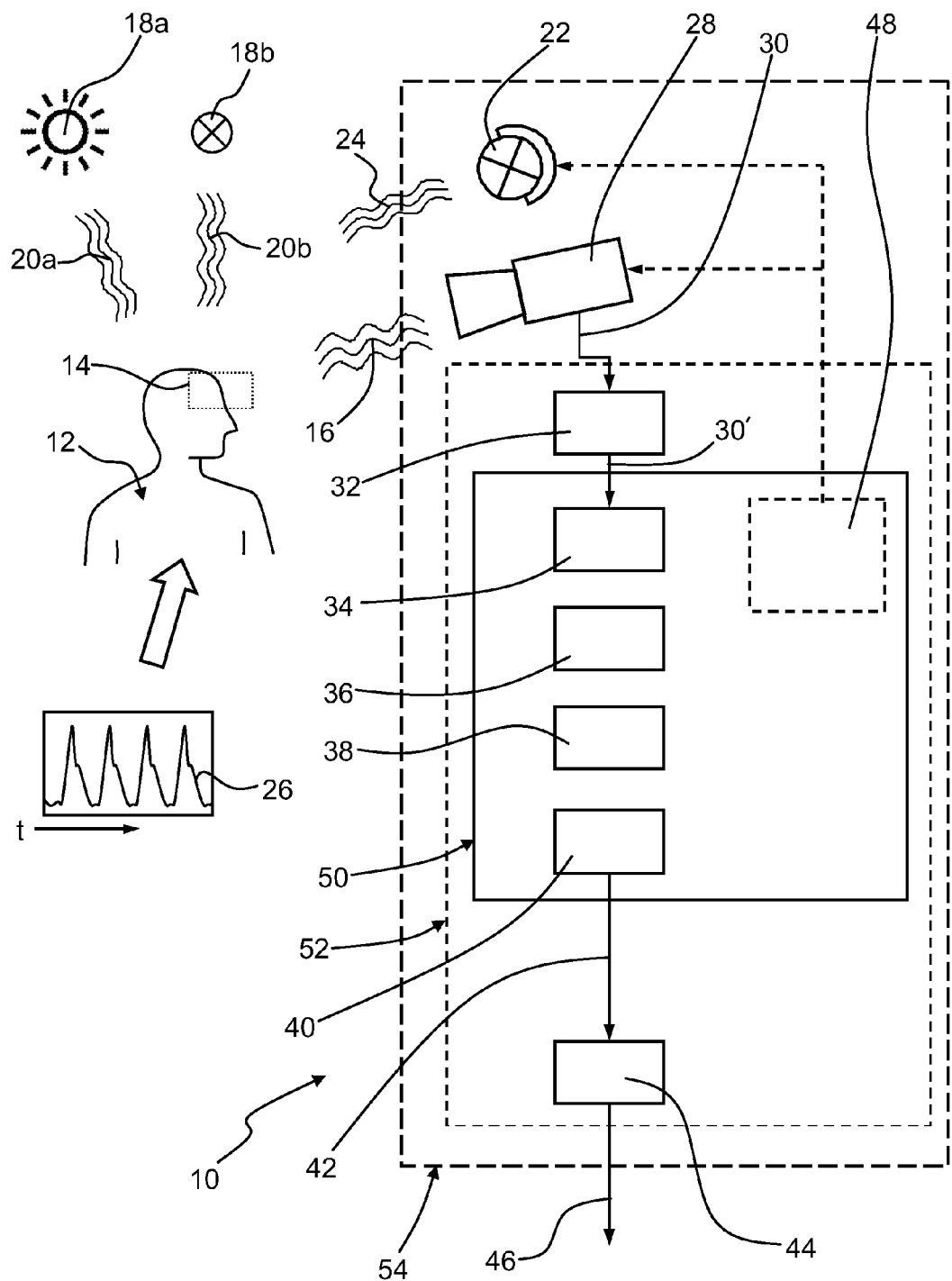
FIG. 1 shows a schematic illustration of a general layout of a device according to the present disclosure.

FIG. 1 shows a schematic illustration of a device for extracting physiological information which is denoted by a reference numeral 10. For instance, the device can be utilized for recording image frames representing a remote subject 12 or at least a portion of the subject 12 for remote PPG monitoring. In this connection, a region of interest 14 in the subject 12 can be addressed when monitoring. The region of interest can comprise, by way of example, a forehead portion, a face portion or, more generally, a skin portion of the subject 12. The recorded data, for instance, a series of image frames, can be derived from electromagnetic radiation 16 reflected by the subject 12. Possibly, under certain conditions, at least part of the electromagnetic radiation could be emitted or transmitted by the subject 12 itself. Radiation transmission may occur when the subject 12 is exposed to strong illumination sources shining through the subject 12. Radiation emission may occur when infrared radiation caused by body heat is addressed and captured. However, for remote PPG applications, a huge portion of the electromagnetic radiation 16 to be captured can be considered radiation reflected by the subject 12. The subject 12 can be a human being or an animal, or, in general, a living being. Furthermore, the subject 12 can be considered a part of a human being highly indicative of a desired signal.

A source of radiation, such as sunlight 18a or an artificial radiation source 18b, also a combination of several radiation sources can affect or impinge on the subject 12. The radiation source 18a, 18b basically emits incident radiation 20a, 20b striking the subject 12. In addition, or in the alternative, the device 10 can also comprise or make use of an internal source of electromagnetic radiation 22. In other words, the device 10 can comprise at least one source of illumination which emits and directs incident radiation 24 to the subject 12. The internal source of radiation 22 can be configured for directing radiation having defined characteristics to the subject 12, in particular radiation belonging to a defined spectral portion. Since in accordance with an embodiment of the disclosure, three distinct spectral portions are captured and processed, according to another aspect of this embodiment it is preferred that the internal source of electromagnetic radiation 22 "matches" these spectral portions of which the at least one indicative signal component and the at least one auxiliary signal component are composed.

For extracting physiological information from the captured data, for instance, a sequence of image frames, a defined part or portion of the subject 12 such a the region of interest 14 can be detected by a sensor unit 28. The sensor unit 28 can be embodied, by way of example, by an optical sensor unit adapted for capturing information belonging to at least one spectral component of the electromagnetic radiation 16. In a fairly simple embodiment, the sensor unit 28 can be embodied by a camera or a set of cameras.

Needless to say, the device 10 can also be adapted to process input signals, namely an input data stream, already recorded in advance and, in the meantime, stored or buffered. As indicated above, the electromagnetic radiation 16 can contain a continuous or discrete characteristic signal which can be highly indicative of at least one vital parameter 26. The characteristic signal can be embodied in an input data stream 30.

Generally, the characteristic signal is considered to contain a considerably constant (DC) portion and an alternating (AC) portion superimposing the DC portion. Applying signal processing measures, the AC portion can be extracted and, furthermore, compensated for disturbances. For instance, the AC portion of the characteristic signal can comprise a dominant frequency which can be highly indicative of the subject's 12 vascular activity, in particular the heart beat. Still, the characteristic signal, in particular the AC portion, can be indicative of further vital parameters. In this connection, the detection of blood oxygen saturation is an important field of application. As indicated above, basically, blood oxygen saturation-representative values can be computed taking into account the behavior of the AC portion of the characteristic signal at distinct spectral portions thereof. In other words, a degree of blood oxygen saturation can be reflected in different radiation absorbance at blood vessels. Furthermore, one can make use of the fact that the difference in absorbance due to the grade of oxygenation also varies significantly across different spectral portions. Moreover, also the DC portion of the signal can be utilized for blood oxygen saturation detection. Typically, the DC component represents the overall light absorption of the tissue, venous blood, and non-pulsatile arterial blood. By contrast, the AC component may represent the pulsatile arterial blood's absorption. Consequently, the determination of blood oxygen saturation $(SO_2)_p$ can be expressed as:

$$S_pO_2 = C \cdot \frac{(AC/DC)_{red}}{(AC/DC)_{infrared}}, \tag{2}$$

where C is a calibration parameter. C may stand for a large variety of calibration parameters applicable to the AC/DC relationship and should therefore not be interpreted in the strict algebraic sense of equation (2). Typically, in prior art measurement devices, C represents a fixed constant value, or a set of fixed constants.

According to the present disclosure an approach directed to an adjustable calibration parameter is utilized. By way of example, another exemplary $S_pO_2$ derivation model can be expressed as:

$$S_pO_2 = C_1 + C_2 \cdot \frac{(AC/DC)_{red}}{(AC/DC)_{infrared}}, \tag{3}$$

where $C_1$ and $C_2$ can be considered calibration parameters of a linear approximation. In an exemplary embodiment, the signal calibration parameter determination can be directed to adjust or adapt the parameter $C_1$. Still, in the alternative, $S_pO_2$ derivation may also be based on value tables deposited in (or accessible by) the device 10. The value tables (or: data bases) may provide for a discrete representation of the relationship between detected PPG signals and the desired calibration parameter. Also in that case an adaptable calibration parameter may be applied to improve the accuracy of the vital parameter determination.

It should be understood that the equations (2) and (3) are primarily presented for illustrative purposes. They should not be construed as limiting the scope of the present disclosure. In practice, the skilled person may determine and establish further appropriate $S_pO_2$ derivation models.

The data stream 30 comprising the continuous or discrete characteristic signal can be delivered from the sensor unit 28 to an interface 32. Needless to say, also a buffer means could be interposed between the sensor unit 28 and the interface 32. Downstream of the interface 32, the input data stream 30' can be delivered to a processing module or processing unit 50. The processing unit 50 can be considered a computing device, or at least, part of a computing device driven by respective logic commands (program code) so as to provide for desired data processing. The processing unit 50 may comprise several components or units which are addressed in the following. It should be understood that each component or unit of the processing unit 50 can be implemented virtually or discretely. For instance, the processing unit 50 may comprise a number of processors, such as multi-core processors or single-core processors. At least one processor can be utilized by the processing unit 50. Each of the processors can be configured as a standard processor (e.g., central processing unit) or as a special purpose processor (e.g., graphics processor). Hence, the processing unit 50 can be suitably operated so as to distribute several tasks of data processing to adequate processors. In accordance with an advantageous embodiment, the processing unit 50 comprises a signal decomposing unit 34 configured for processing the input data stream 30' such that the at least one indicative signal component and the at least one auxiliary signal component can be derived therefrom. As indicated above, each of the at least one indicative signal component and the at least one auxiliary signal component can be delivered to the processing unit 50 via a separate signal channel (in the data stream 30'). In the alternative, however, the at least one indicative signal component and the at least one auxiliary signal component can be embedded in a single channel to which component extraction measures have to be applied.

The processing unit 50 may further comprise a signal comparator 36 for detecting a characteristic signal discrepancy between at least one of the at least one indicative signal component and the at least one auxiliary signal component wherein the signal discrepancy is related to a physiological state of the subject 12 to be observed. As indicated above, the signal comparator 36 can be configured for processing the respective signal components such that signal correlation-related values can be determined. To this end, cross-correlation or similar correlation measures can be applied to the signal components. A cross-correlation value can be indicative of a time lag, time delay or, in other words, a temporal gap between the at least one auxiliary signal component and at least one of the at least one indicative signal components. The detection of the temporal gap basically allows for the determination of an adjusted calibration parameter. In this way, posture-related signal deviations can be compensated. This approach is based on the idea that a constant calibration parameter which is applicable for contact blood oxygen saturation detection cannot be transferred into remote blood oxygen saturation measurement environments. For remote monitoring, it has to be considered that the subject 12 sometimes changes posture. A posture change does not necessarily have to involve a relative orientation change of the subject 12 with respect to the sensor unit 28.

It would be therefore advantageous to be aware of a current posture of the subject 12. However, an instant immediate detection of a current posture of the subject 12 would require huge computational efforts or, alternatively, manual intervention by an operator of the device. Therefore, according to a preferred aspect, a beneficial approach seeks for mediately detecting and accounting for posture-related disturbances. To this end, a preferred embodiment can make use of the fact that posture changes differently influence the detected signals in distinct spectral signal portions. The signal discrepancy detected by the signal comparator 36 is therefore considered indicative of an actual posture of the subject 12. The signal discrepancy can be utilized for adjusting the calibration parameter.

To this end, the processing unit 50 comprises a calibration processor 38 configured for determining a signal calibration parameter under consideration of the detected signal discrepancy. Determining the signal calibration parameter may involve computing a current signal calibration parameter on the basis of a currently detected signal discrepancy and a given relationship between the signal discrepancy and a respective adjustment of the calibration parameter.

The processing unit 50 can further comprise a signal analyzing unit 40 for detecting the at least one vital parameter under consideration of the calibration parameter. The analyzing unit 40 can be configured for computing the at least one vital parameter on the basis of an adjusted calibration parameter and a general relationship between the at least one indicative signal component and the vital parameter of interest.

Eventually, a processed data stream 42 can be generated by the processing unit 50. Downstream of the processing unit 50, an (output) interface 44 can be provided to which the processed data 42 can be delivered. Both interfaces 32, 44 can be embodied by the same (hardware) connectors. Via the interface 44, output data 46 can be made available for further analysis and/or for display measures.

The processing unit 50 can further comprise a monitoring controller 48 which can be configured for selectively controlling at least one of the sensor unit 28 and the integrated source of radiation 22.

The processing unit 50 as well as the interfaces 32, 44 can be embodied in a common processing apparatus or housing 52. Reference numeral 52 can also describe a virtual system boundary. Still, also the sensor unit 28 and the at least one integrated source of radiation 22 can be integrated into the common processing housing 52. A potential overall system boundary of the device 10 is denoted by a reference numeral 54. It should be understood that the device 10 can also be implemented as a distributed device. For instance, at least the sensor unit 28 and/or the source of electromagnetic radiation 22 can be positioned separate or distant from the processing unit 50. Moreover, functional entities of the processing unit 50 can be implemented in distributed processing devices which can be connected via cable or wireless connections or networks.

Figure 2:
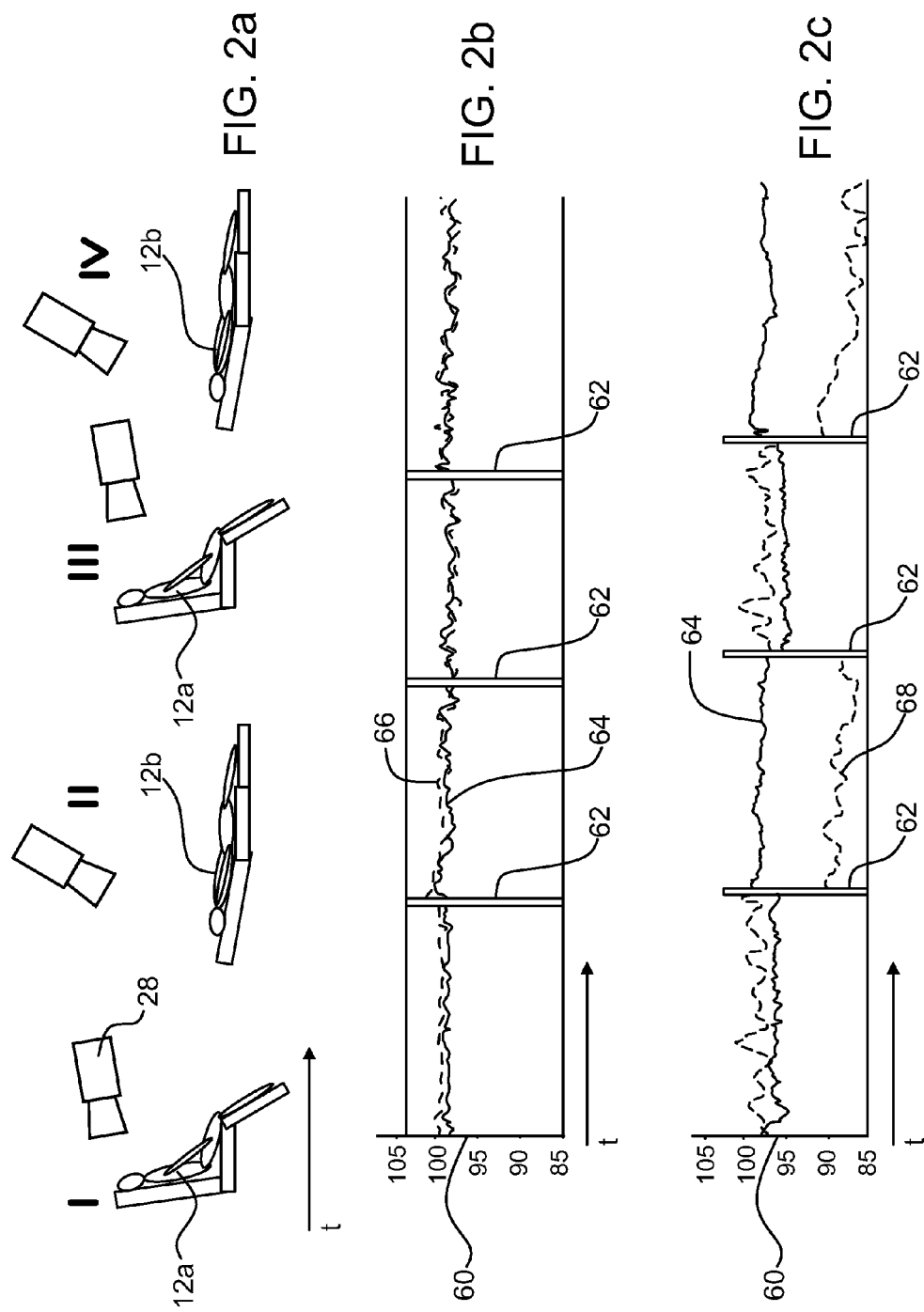

FIG. 2a illustrates an exemplary representation of the subject 12 changing posture when being monitored by the sensor unit 28 for vital parameter detection. As indicated by reference numeral 12a, the subject 12 can be monitored in a seated position. As indicated by a reference numeral 12b, the subject 12 can be monitored in a lying position. In an exemplary measurement which is also addressed further below in connection with FIGS. 2b and 2c, a series of postures may involve I—the subject 12 sitting, II—the subject 12 lying, III—the subject 12 (again) sitting, and IV—the subject 12 (again) lying. In this elucidating example, throughout the series I, II, III, IV the relative position and orientation between the sensor unit 28 and the subject 12 (more precisely: the region of interest 14) remain substantially constant. The same may apply to the source of radiation 22 (not shown in FIG. 2a).

FIG. 2b and FIG. 2c illustrate diagrams of detected blood oxygen saturation representative values. In each of the diagrams, an axis of abscissas represents time t. An ordinate axis 60 represents computed $S_pO_2$ values. Both diagrams in FIG. 2b and FIG. 2c are based on similar monitoring procedures which are illustrated in FIG. 2a. That is, the subject 12 is monitored over a series of periods I, II, III, IV in each of which the subject 12 basically remains in position which are interrupted by defined posture changes. The posture changes are indicated by vertical lines 62 in the diagrams shown in FIG. 2b and FIG. 2c.

In FIG. 2b a signal 64 represents a reference value obtained through contact measurement via a contact probe attached to a finger tip of the subject 12. Furthermore, a forehead control reference value 66 is shown in FIG. 2b. The respective signal is obtained via contact measurement applying a contact probe to the forehead of the subject 12. As indicated above, the forehead portion may act as the region of interest 14 which is monitored by the sensor unit 28. In FIG. 2b it is clearly shown that both signals 64, 66 show basically the same results, even though different regions of interest have been utilized, namely the finger tip for the signal 64 and the forehead portion for the signal 66.

The diagram shown in FIG. 2c also provides for a representation of the signal 64 representing a reference value obtained through contact measurement at a finger tip of the subject 12. By contrast, the signal 68 represents $S_pO_2$ values obtained through remote monitoring making use of an unobtrusive remote sensor unit 28. As already indicated above, depending on an actual posture of the subject 12, huge signal deviations with respect to the reference signal 64 are present in the remote signal 68 which has been extracted from data obtained through remotely monitoring the forehead portion of the subject 12. It is clearly visible that for remote monitoring, a given posture of the subject 12 significantly influences the quality of the extracted signal 68. It is worth mentioning in this connection that the signal 68 has been computed without making use of the adjustable calibration parameter. In other words, the signal 68 has been computed under consideration of a well-established constant calibration parameter which is deemed to be sufficient for contact $S_pO_2$ measurement.

It is worth mentioning in this connection that the present disclosure may relate to both contact probes and remote probes. As used herein, the terms "remote" and "remotely" may refer to unobtrusive contactless vital signal monitoring, for instance to camera based monitoring devices. However, these terms may also refer to vital signal monitoring devices making use of contact probes, wherein the sensor and the source of radiation are spaced apart from each other at a considerable distance. More generally, the present disclosure may relate to monitoring devices and systems, wherein the radiation emitted towards the subject and eventually re-emitted by the subject has to pass a considerable distance between the radiation source and the detector (or: sensor unit). Furthermore, assuming that according to some aspects wide field illumination can be utilized, a variety of distances between the detector and respective (local) portions of the illumination source (from which respective radiation portions are emitted) has to be taken into account.

Figure 3:
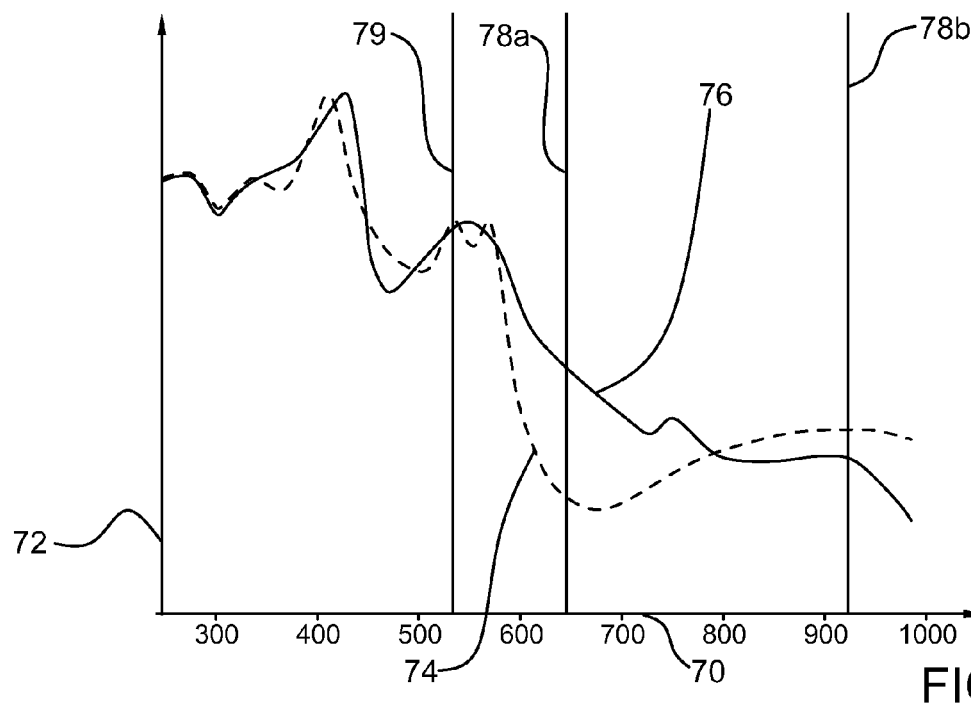
FIG. 3 shows an exemplary light absorbance diagram illustrating absorption of light in blood dependent on wavelength properties.

FIG. 3 shows a diagram representing radiation absorbance in blood in relation to wavelength of incident radiation. An axis of abscissas 70 represents wavelength (in nm). An ordinate axis 72 represents absorbance. As indicated above, radiation absorption capability of blood is dependent on an actual oxygen saturation of the blood. In this connection, reference numeral 74 denotes an exemplary graph representing absorption capability of (fully) oxygenated blood ($HbO_2$). By contrast, reference numeral 76 denotes a graph representing de-oxygenated blood (Hb). Pulse oximetry makes use of this relationship by applying light at different wavelengths to the subject 12 and detecting a respective response which is basically influenced by a current radiation absorbance or reflectance.

In FIG. 3, reference numeral 78a indicates a wavelength portion which may serve as a first indicative spectral portion a first signal component of the at least one indicative signal component can represent. The first indicative spectral portion 78a can comprise visible light, in particular, red light. A second indicative spectral portion which can be represented by the second signal component of the at least one indicative signal component can be indicated by the reference numeral 78b. The second indicative spectral portion 78b can comprise infrared (or: near-infrared) signals. As indicated above, at least one auxiliary signal component can be used for detecting the characteristic signal discrepancy. In FIG. 3, a reference numeral 79 indicates a respective auxiliary spectral portion. The auxiliary spectral portion 79 can be composed of green light, by way of example. It should be noted in this connection that the respective portions or segments 78a, 78b, 79 should not be understood or regarded in a limited way as "monochrome" segments in the strict sense of the term "monochrome". Each of the reference numerals 78a, 78b, 79 may also stand for a wavelength interval or a respective wavelength distribution. It is worth pointing out in this context that in some exemplary embodiments the source of radiation 22 utilized in the device 10 may be a broadband illumination source covering a considerable wavelength range which comprises the spectral portions 78a, 78b, 79. Still, however, the sensor unit 28 can be configured for selectively sensing incident radiation at defined wavelengths or defined wavelength portions.

However, for remote pulse oximetry approaches, further disturbances have to be considered. Given that prior art contact measurement devices basically make use of transmitted light and that, in turn, remote vital signal monitoring is basically directed to capture reflected light, attention has to be put on radiation penetration mechanisms which are considered to be at least partially responsible for the deviating signals obtained through remote measuring, see FIG. 2c.

Figure 4A:
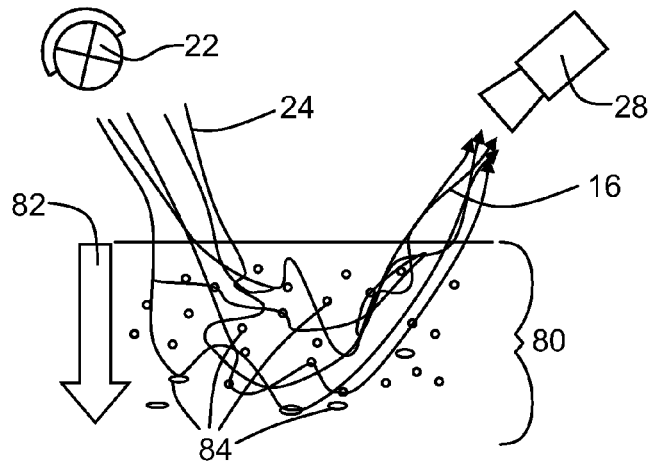
FIGS. 4a, 4b show schematic illustrations of light absorbance and reflectance at a subject's skin tissue.
Figure 4B:
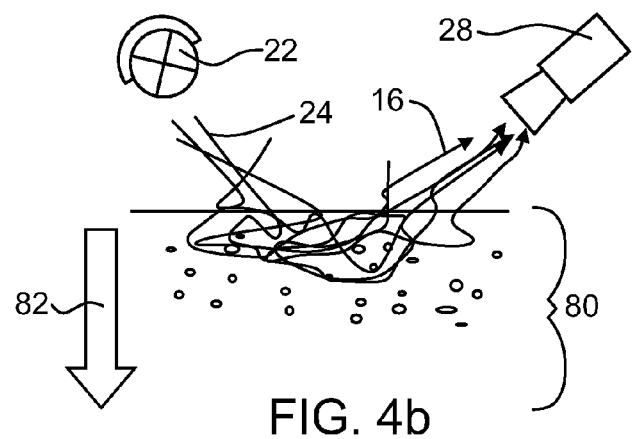

FIG. 4a and FIG. 4b illustrate absorbance and reflectance mechanisms for radiation at a skin tissue 80 of the subject 12. A penetration depth of incident radiation 24 into the skin tissue 80 is indicated by a block arrow 82. In contrast to contact measurements, remote measurements typically comprise partial reflections of incident radiation 24 at the surface of the skin tissue 80. Radiation portions which are reflected at the top surface of the skin tissue 80 are considered non-indicative of the desired vital parameters. Consequently, the electromagnetic radiation 16 reflected by the subject 12 of interest may comprise a non-indicative portion attributable to surface reflection radiation. Still, a huge portion of the incident radiation 24 penetrates into the skin tissue 80. It is reminded in this connection that incident radiation 24 which is absorbed by the subject's 12 skin is basically not detectable. By contrast, merely the reflected portion 16 of the radiation can be captured by the sensor unit 28. It should be further noted that radiation absorption in the skin tissue 80 is attributable to several absorption components. As illustrated in FIG. 3, blood absorption forms a certain share of the overall skin tissue 80 absorption. However, also melanin absorption contributes in overall absorption of incident radiation 24 at the skin tissue 80 of the subject 12. Melanin absorbance typically decreases with increasing wavelength. For the sake of illustration, a typical shape of a path of radiation rays which are emitted by the radiation source 22, re-emitted by the subject 12 and, eventually, detected by the sensor unit 28 can be referred to as "banana" shaped.

It can be therefore assumed that an auxiliary spectral portion being composed of radiation having considerably shorter wavelength cannot penetrate into the skin tissue 80 of the subject 12 as deep as any of the at least one indicative spectral portions being composed of radiation of longer wavelength. It is considered beneficial to detect the auxiliary signal component along with the at least one indicative signal component so as to obtain a further signal which is, in connection with the at least one indicative signal component, indicative of a current posture (or: orientation) of the subject 12. This approach can make use of the fact that posture changes may differently influence distinct wavelength portions of the reflected radiation 16.

FIG. 4a may provide a representation of an absorbance and reflectance behavior of the skin tissue 80 when the incident radiation is representative of at least one of the first and second indicative spectral portion. The skin tissue 80 may comprise several constituents 84, for instance, blood vessels and/or melanin constituents. Given that for long-wavelength radiation blood absorption and also melanin absorption is considerably low, the incident radiation 24 can reach a reasonably great depth. In FIG. 4b which illustrates incident radiation 24 representing the auxiliary spectral portion of which the auxiliary signal component is composed, the incident radiation 24 can penetrate the skin tissue 80 to a lesser degree. Huge portions of the long-wavelength radiation are absorbed in shallow regions of the skin tissue 80, due to the greater absorbance of the auxiliary spectral portion. In FIG. 4b, the radiation rays form a shallower "banana" shape than in FIG. 4a. In other words, the radiation rays representing the auxiliary spectral portion may not penetrate the subject's 12 skin tissue as deep as the radiation rays which represent the at least one of the first and the second indicative spectral portion, refer to FIG. 4a.

It is worth pointing out that the monitoring environment underlying FIGS. 4a and 4b does not necessarily has to comprise a remote radiation source 22 and a remote sensor unit 28. By contrast, the monitoring environment can also make use of a contact radiation source (illumination source) 22 and a contact sensor unit 28 which may be, for instance, implemented in a single transceiver probe unit. Also in this connection basically similar signal characteristics (in terms of the general relation between wavelength and penetration depth) may be expected. It should be further noted that the illustrations provided in FIG. 4a and FIG. 4b may be regarded as partial representations of selected wavelength portions chosen from a wide wavelength band. This applies in particular when broadband illumination sources are utilized.

Figure 5A:
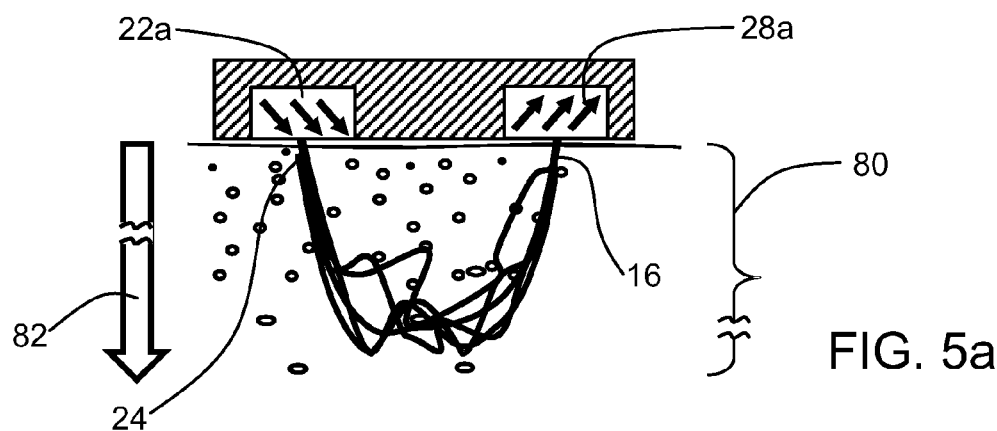
FIGS. 5a, 5b show further schematic illustrations of light absorbance and reflectance at a subject's skin tissue.
Figure 5B:
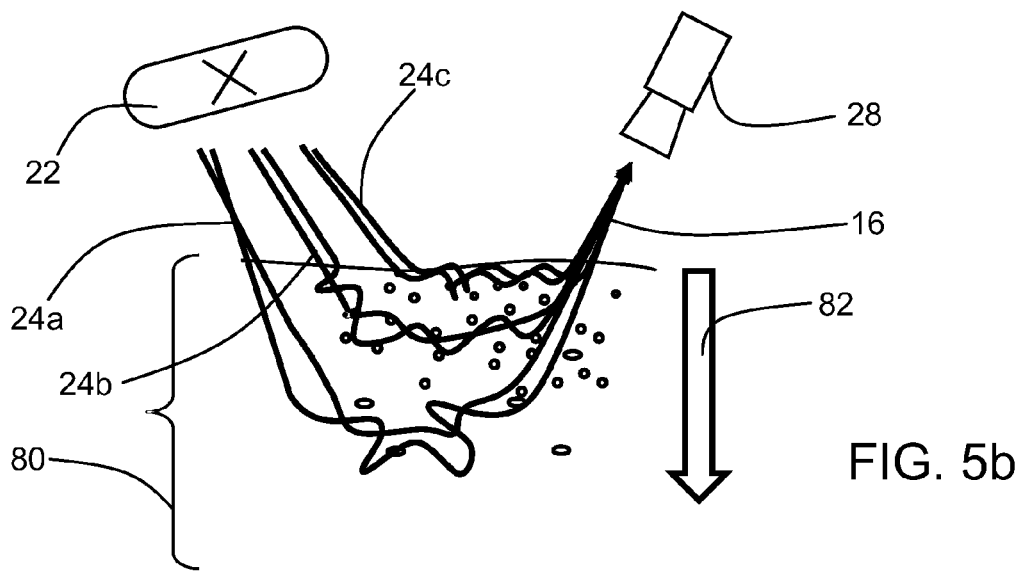

FIG. 5a and FIG. 5b show further schematic illustrations of radiation absorbance, reflectance and re-emission at the skin tissue 80 of the subject 12. In FIGS. 5a and 5b, the radiation rays do not necessarily represent various distinct spectral portions. At least the incident radiation portions 24 may comprise basically the same spectral composition. The radiation rays which may involve an incident radiation portion 24 and a reflected radiation portion 16 may rather represent a relationship between a given distance between the radiation source 22 and the sensor unit 28, and a penetration depth 82 of the radiation rays into the skin tissue 80 of the subject 12. In other words, the depth of the respective "bananas" may be basically dependent on the distance between the radiation source 22 and the sensor unit 28.

FIG. 5a exemplifies a monitoring environment in which a contact transceiver probe is utilized. To this end, a contact radiation source 22a and a contact sensor unit 28a may be directly attached to the surface of the skin tissue 80. For contact transceiver units, incident radiation 24 emitted by the radiation source 22a may typically penetrate deep into the subject's 12 skin tissue 80. Consequently, the brace 80 indicating the skin tissue dimension and the block arrow 82 indicating the depth are shown in FIG. 5a in broken view representation. For some contact monitoring approaches, the penetration depth may come to at least 1 mm, typically up to the range of several millimeters.

FIG. 5b illustrates a remote monitoring environment in which the source of radiation 22 is embodied by a wide field illumination source. Emitted radiation 24 can therefore comprise several emitted radiation portions 24a, 24b, 24c which may represent various distances between the radiation source 22 and the sensor unit 28. Typically, a relatively short distance between the radiation source 22 and the sensor unit 28 or, respectively, a relatively short path a radiation ray has to travel may be reflected in a shallow penetration depth 82 in the skin tissue 80, refer to reference numeral 24c. By contrast, a relatively long distance between the radiation source 22 and the sensor unit 28 or, respectively, a relatively long path a radiation ray has to pass may be reflected in a deep penetration depth 82 in the skin tissue 80, refer to reference numeral 24a.

Generally, remote illumination and signal detection may involve considerably shallow penetration depths when compared to contact monitoring (FIG. 5a). For instance, in some non-contact monitoring embodiments, the penetration depth may come to no more than 1 mm. It is therefore pointed out that the illustrations shown in FIGS. 5a and 5b are not necessarily based on the same scale (in terms of penetration depth).

Figure 6:
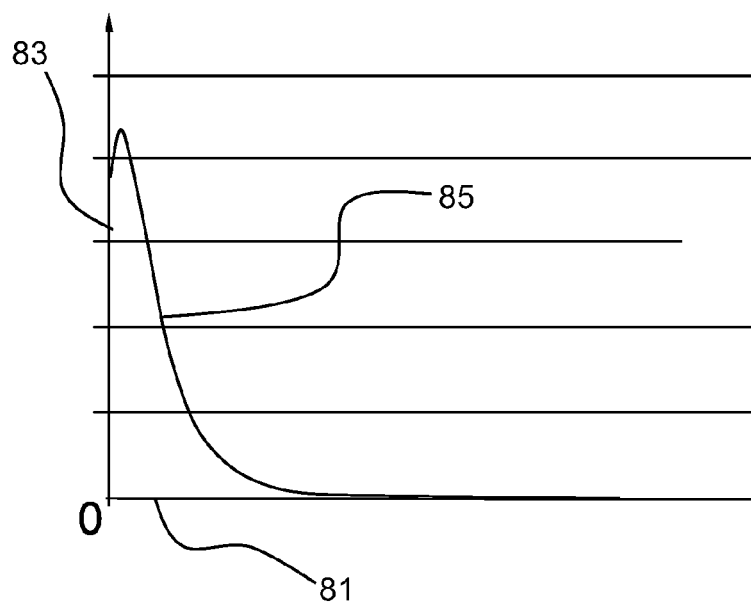
FIG. 6 shows an exemplary intensity diagram exemplifying a general relation between the intensity of detected radiation and a distance between the radiation source and the sensor unit.

FIG. 6 shows an illustrative intensity diagram exemplifying a general relation between the intensity of detected radiation and a distance between the radiation (illumination) source and the sensor unit. Radiation rays emitted from long-distanced sources (ref. to reference numeral 24a in FIG. 5b) which have to travel a longer path are typically attenuated to a greater extent in the subject's 12 skin tissue 80 than radiation rays emitted from short-distanced sources (ref. to reference numeral 24c in FIG. 5b). Attenuation may involve, for instance, absorption and scattering. Consequently, only slight remainders of the long-distance radiation rays can be detected by the sensor unit 28. In other words, long-distance radiation rays can be considered as being underrepresented in the detected (agglomerated) signals while short-distance radiation rays can be considered as being overrepresented in the detected signals. In FIG. 6, an axis of abscissas 81 may represent a distance between the radiation source 22 (or: a respective portion of a wide field illumination source) and the sensor unit 28. An ordinate axis 83 may represent a relative intensity of detected radiation. As illustrated by a signal graph denoted by reference numeral 85, the intensity of detected radiation strongly decreases with increasing distance.

Considered in conjunction, FIGS. 3 to 6 illustrate that the reflection/absorption mechanisms of incident radiation (including penetration depth, reflection intensity, etc.) typically may be dependent on spectral characteristics of the radiation and on a given distance between the source of radiation 22 and the sensor unit 28.

FIG. 7a and FIG. 7b represent characteristic signals 86 comprising respective signal components which are obtained through remote measurement. The diagram of FIG. 7a is based on a measurement in which the subject 12 is in a first posture, for instance in a sitting posture. By contrast, the diagram of FIG. 7b is based on a measurement in which the subject 12 is in a second posture, for instance in a lying posture.

Each of the diagrams represents three signal components. The signal components 88, 90 can be considered indicative signal components. By way of example, the indicative signal component 88 can represent red signals. The indicative signal component 90 can represent infrared signals. A third signal component 92 can be considered an auxiliary signal component which may, by way of example, represent green signals. Each of the signal components 88, 90, 92 can be highly indicative of a certain spectral portion of electromagnetic radiation, refer to reference numerals 78a, 78b, 79 in FIG. 3.

As indicated above, vital parameter detection is typically based on the indicative signal portions 88, 90. The auxiliary signal component 92 is used in an immediate way since, based on this component, a posture-related adjustment of a calibration parameter can be performed. In FIG. 7a, the signal components 88, 90, 92 are "ganging". This may imply that characteristic signal values of the signal components 88, 90, 92 are basically synchronized. Extreme values, for example, local minima 94 of the first indicative signal component 88, local minima 96 of the second indicative signal component 90, and local minima 98 of the auxiliary signal component 92 basically occur in unison. None of the signal components 88, 90, 92 is significantly lagging or running ahead.

In FIG. 7b, the auxiliary signal component 92 is considerably lagging behind, refer in this connection to the arrow t denoting time. An actual temporal discrepancy or gap 100 can be determined by applying correlation measures to the signal components 88, 90, 92. As indicated above, cross-correlation can be applied for detecting a present temporal discrepancy of the at least one auxiliary signal component 92 with respect to at least one of the first indicative signal component 88 and the second indicative signal component 90. To this end, extreme values 94, 96, 98 of the respective signals can be detected, tracked and processed so as to determine an actual time delay. It should be understood that, apart from cross-correlation analysis, further approaches can be utilized for estimating a temporal discrepancy 100 between the respective signal components.

Figure 8:
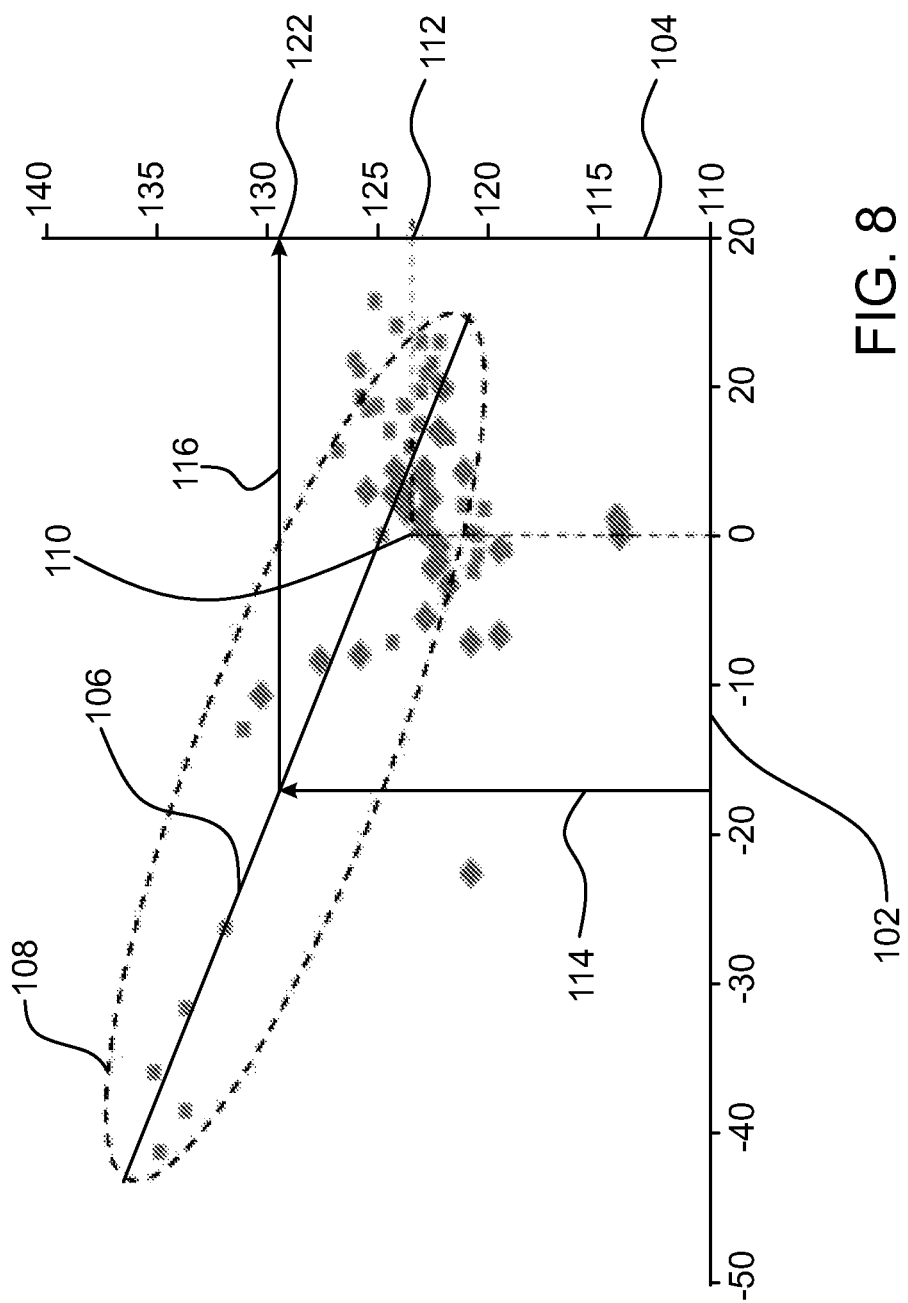
FIG. 8 illustrates a set of signal values representing a signal discrepancy related to a posture of a monitored subject.

FIG. 8 shows an exemplary reference plot elucidating a relationship between detected signal discrepancy values and corresponding adjusted (optimum) calibration parameters. An axis of abscissas 102 may represent a detected time lag between the auxiliary signal component 92 and the indicative signal component 90, refer to FIGS. 7a and 7b. In other words, each of the entities shown in FIG. 8 may represent a detected time lag (in ms) between a green signal component and an infrared signal component in a (single) measurement. For each of the measurements represented in FIG. 8 also a contact reference measurement has been conducted. In this way, when comparing the respective contact measurement and remote measurement, an adjusted calibration parameter considered optimal for the actual remote measurement condition (for instance, a given posture) can be computed. Posture changes may result in an increasing time lag between the respective signal components and can therefore require an adjustment of the calibration parameter.

In FIG. 8, an ordinate axis 104 may represent qualitative and/or quantitative values of a resulting calibration parameter. Reference numeral 108 denotes an exemplary range in which respective values characterized by a given time lag and a resulting optimum calibration parameter are expected to be present (disregarding outliers). A regression line 106 can be computed based on a given set of respective entities. The regression line 106 can be a straight line. In the alternative, the regression line 106 could be embodied by a regression curve, depending on an underlying regression model.

Given that no significant time lag is present (zero-value on the axis 102), a neutral calibration parameter 112 can be chosen which may basically correspond to the respective (constant) calibration parameter applied to contact measurements. For a given time lag input value (refer to the arrow 114) a corresponding adjusted calibration parameter 122 can be determined under consideration of the given regression line or curve 106, refer to the arrow 116.

Figure 9B:
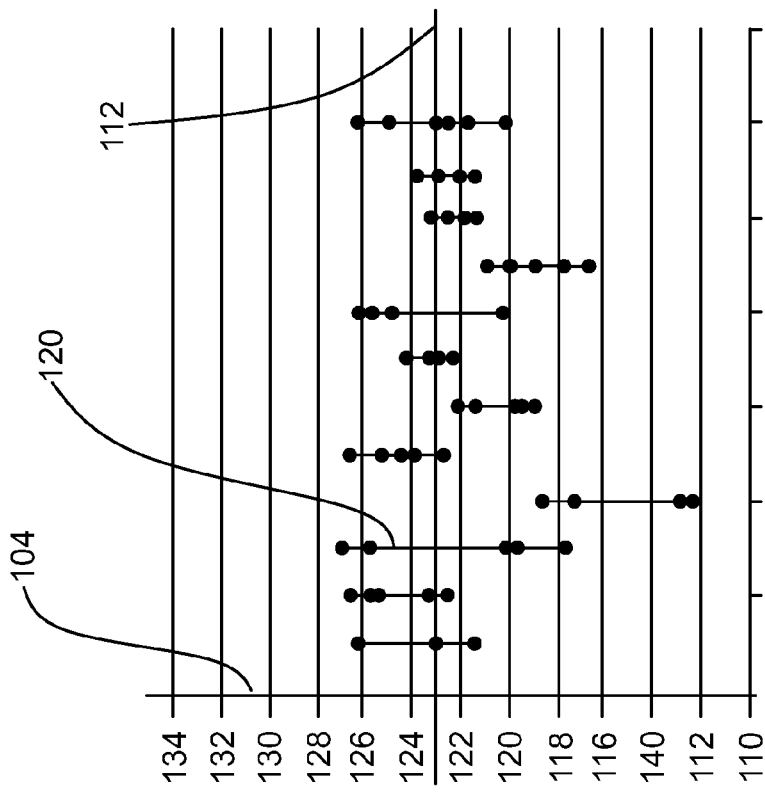
FIG. 9b represents a corresponding set of vital signal parameter-indicative values each of which having a certain range which have been computed under consideration of a calibration parameter adjustment approach.
Figure 9A:
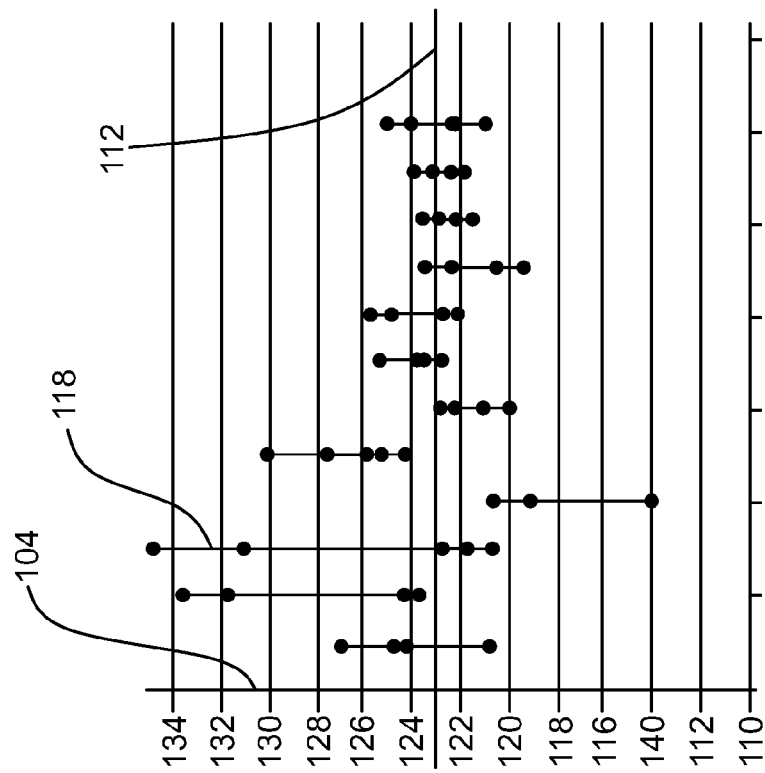
FIG. 9a illustrates a set of vital signal parameter-indicative values each of which having a certain range which have been processed under consideration of a fixed calibration parameter approach.

FIG. 9a and FIG. 9b illustrate respective ranges of an optimally adjusted calibration parameter for a set of 12 remote measurements each of which directed to a different subject which changed posture from time to time. As indicated above, also contact reference measurements have been performed. FIG. 9a represents respective calibration parameter spreads (or: ranges) 118 for a conventional signal extraction approach giving no attention to temporal time discrepancies between the signal components. By contrast, FIG. 9b is based on an exemplary signal extraction approach in accordance with the present disclosure which makes use of the fact that a detected temporal signal discrepancy can be utilized for enhancing the signal quality of the finally derived vital parameter of interest. In each of the FIGS. 7a and 7b, a horizontal line 112 illustrates a neutral calibration parameter typically utilized for contact measurements. The set of spreads of FIG. 9a clearly shows huge deviations. In other words, based on a reference contact measurement assumingly providing empirical truth, some of the spreads 118 in FIG. 9a show that huge corrections would be required for making the detected vital parameter conform to the respective reference vital parameter obtained through contact measurement. Hence, remote signal detection under consideration of a constant calibration parameter is considered inapplicable for many remote monitoring environments.

Based on the same measurement scenarios, FIG. 9b clearly shows an improvement in signal quality. By adopting the adjustable calibration parameter approach, the respective spreads can be reduced in many of the exemplary measurements. By way of example, a huge spread 118 present in FIG. 9a can be transferred into a significantly reduced spread 120 in FIG. 9b by considering the relationship between the detected signal discrepancy and an optimized adjusted calibration parameter.

Figure 10:
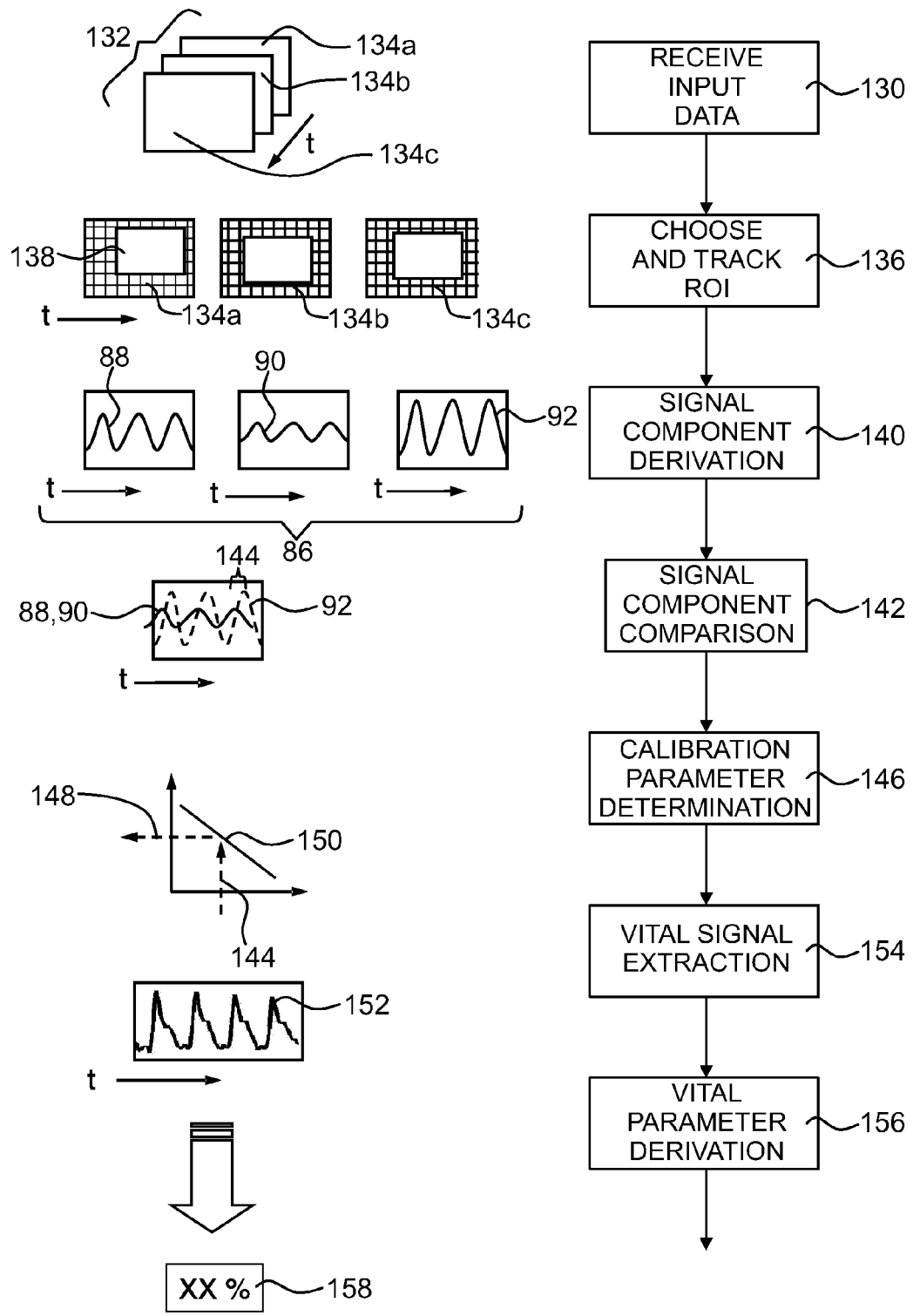
FIG. 10 shows an illustrative block diagram representing several steps of an embodiment of a method in accordance with the disclosure.

Having demonstrated several alternative exemplary approaches covered by the disclosure, FIG. 10 is referred to, schematically illustrating a method for extracting information from detected electromagnetic radiation. Initially, in a step 130 an input data stream or sequence 132 comprising a series of frames 134a, 134b, 134c is received. A time axis is indicated by an arrow t. The input sequence 132 can be delivered from the sensor unit 28, or from a data buffer or storage means. The input data stream can be embodied, by way of example, by a sequence of image frames or, image frame portions, varying over time, or by a respective set of sequences. The image frames can comprise pixel data representative of several spectral portions of radiation.

In a subsequent step 136, a region of interest 138 can be chosen and tracked over time in the frames 134a, 134b, 134c. The region of interest 138 may comprise a representation of a forehead portion of the subject 12 of interest. Since remote monitoring is addressed, relative motion between the subject 12 and the sensor unit 28 has to be expected. Consequently, tracking the region of interest 138 may result in an improved signal quality.

Another step 140 may follow in which signal components 88, 90, 92 are derived from a respective characteristic signal 86 which is embedded in the input sequence 132. By way of example, the signal components 88, 90, 92 can be considered distinct color (or: spectral) channels within the characteristic signal 86. The characteristic signal 86 can be indicative of visible radiation and of infrared radiation. For instance, the characteristic signal 86 can be composed of a red channel, a green channel and, if any, a blue channel, and may further comprise an infrared channel. The signal components 88, 90 can be considered indicative signal components since they are indicative of a vital parameter of interest. The signal component 92 can be considered an auxiliary signal component since based on this component a posture-related signal discrepancy can be detected.

To this end, a signal component comparison step 142 may follow in which a signal discrepancy between the auxiliary signal component and at least one of the indicative signal components 88 and 90 is detected. The signal discrepancy can be represented by a time lag between prominent features in the auxiliary signal component 92 and at least one of the indicative signal components 88, 90.

In a subsequent determination step 146 an adjusted calibration parameter 148 can be determined on the basis of the detected signal discrepancy 144 and a given relationship 150. The relationship 150 can be empirically determined. The relationship 150 can be obtained through reference measurements involving contact measurements and remote measurements. The relationship 150 may stand for a correlation line or curve obtained through statistical considerations on the basis of a set of exemplary reference values.

In another step 154, signal extraction measures may follow directed to extraction of a vital signal 152 under consideration of the adjusted calibration parameter 148. In this way, posture-related disturbances can be reduced.

Further on in another signal processing step 156, a desired vital parameter 158 can be derived from the (at least one) vital signal 152 derived from the characteristic signal 86.

By way of example, the present disclosure can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases. Needless to say, in an embodiment of the method in accordance with the disclosure, several of the steps described herein can be carried out in changed order, or even concurrently. Further, some of the steps could be skipped as well without departing from the scope of the invention.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A device for extracting physiological information from detected electromagnetic radiation emitted or reflected by a subject, comprising:
   a photoplethysmography (PPG) camera configured to capture electromagnetic radiation emitted or reflected by a subject at a distance away from the subject;
   a computer configured to receive a data stream derived from the captured electromagnetic radiation, the data stream comprising a continuous or discrete characteristic signal including physiological information indicative of at least one vital parameter, the characteristic signal comprising at least one indicative signal component representative of a detected spectral portion indicative of the at least one vital parameter, the data stream at least sectionally comprising at least one auxiliary signal component detected along with the at least one indicative signal component, the at least one auxiliary signal component being representative of a distinct spectral portion,
   wherein the computer includes at least one computer processor including:
   a signal comparator programmed to detect a characteristic signal discrepancy between the at least one indicative signal component and the at least one auxiliary signal component, the signal discrepancy being related to a posture of the subject;
   a calibration processor programmed to determine a signal calibration parameter based on the detected signal discrepancy; and
   an analyzing processor programmed to determine the at least one vital parameter based on the at least one indicative signal component and the calibration parameter.

2. The device as claimed in claim 1, wherein the signal discrepancy is a temporal signal discrepancy representative of the posture of the subject.

3. The device as claimed in claim 1, wherein the signal discrepancy is a temporal signal discrepancy representing a time delay between the at least one of the at least one indicative signal component and the at least one auxiliary signal component.

4. The device as claimed in claim 1, wherein the signal discrepancy is a signal form discrepancy representing differences in waveform between the at least one of the at least one indicative signal component and the at least one auxiliary signal component.

5. The device as claimed in claim 1, wherein the at least one vital parameter is a parameter representing cardiovascular activity.

6. The device as claimed in claim 1, wherein the at least one vital parameter is selected from the group consisting of oxygen saturation, heart beat, heart rate, heart rate variability, Traube-Hering-Mayer waves, and respiration rate.

7. The device as claimed in claim 1, wherein the calibration parameter is an adaptive calibration parameter, and wherein the at least one processor is programmed to compute the calibration parameter based on statistical adjustment computation measures applying the detected signal discrepancy.

8. The device as claimed in claim 1, wherein the at least one processor is further programmed to detect the signal discrepancy by applying a correlation computation to the at least one of the at least one indicative signal component and the at least one auxiliary signal component.

9. The device as claimed in claim 1, wherein the characteristic signal comprises at least two indicative signal components, wherein a first signal component is representative of a first indicative spectral portion and wherein a second signal component is representative of a second indicative spectral portion.

10. The device as claimed in claim 9, wherein the at least one auxiliary signal component is representative of an auxiliary spectral portion, and wherein the auxiliary spectral portion and at least one of the first indicative spectral portion and the second indicative spectral portion are chosen such that different respective absorption and reflection characteristics appear in an observed tissue of the subject.

11. The device as claimed in claim 1, wherein the PPG camera includes a defined response characteristic of at least two defined spectral distributions.

12. The device as claimed in claim 1, further comprising at least one light source of electromagnetic radiation configured for directing radiation to the subject from a distance, the source configured to generate spectra radiation portions comprising visible radiation and infrared radiation.

13. A pulse oximetry device for extracting physiological information, comprising:
   at least one light source configured to direct light radiation to the subject from a distance, the light source configured to generate light radiation spectra portions comprising visible radiation and infrared radiation;
   a photoplethysmography (PPG) camera configured to detect the visible radiation and the infrared radiation from the at least one light source reflected by the subject at a distance from the subject;
   a data processing system including computer memory and at least one processor programmed to:
   receive a data stream derived from the detected visible and infrared radiation, the data stream comprising a characteristic signal including physiological information indicative of at least one vital parameter, the characteristic signal comprising at least two indicative signal components representative of detected spectral portions indicative of the at least one vital parameter, the data stream at least sectionally comprising at least one auxiliary signal component, the at least one auxiliary signal component being representative of a distinct spectral portion;
   detect a characteristic signal discrepancy between at least one of the at least two indicative signal components and the at least one auxiliary signal component related to posture of the subject,
   determine an adaptive signal calibration parameter based on the detected signal discrepancy; and
   determine the at least one vital parameter based on the at least two indicative signal components and the adaptive calibration parameter.

14. The device as claimed in claim 13, wherein the signal discrepancy is a temporal signal discrepancy representing a time delay between the at least one of the at least two indicative signal components and the at least one auxiliary signal component.

15. The device as claimed in claim 13, wherein the at least one processor is programmed to compute the calibration parameter based on statistical adjustment computation measures applying the detected signal discrepancy.

16. A method for extracting physiological information, the method comprising:
   with a photoplethysmography (PPG) camera positioned at a distance from a subject, capturing electromagnetic radiation emitted from or reflected by the subject;
   with an interface, receiving a data stream derived from detected electromagnetic radiation, the data stream comprising a characteristic signal including physiological information indicative of at least one vital parameter, the characteristic signal comprising at least one indicative signal component representative of a detected spectral portion indicative of the at least one vital parameter, the data stream at least sectionally comprising at least one auxiliary signal component representative of a distinct spectral portion,
   with at least one processor, detecting a characteristic signal discrepancy between the at least one indicative signal component and the at least one auxiliary signal component, the discrepancy being indicative of a posture of the subject,
   with the at least one processor, determining a signal calibration parameter based on the detected signal discrepancy; and
   with the at least one processor, determining the at least one vital parameter based on the at least one indicative signal component and the calibration parameter.

17. The method as claimed in claim 16, further comprising:
   with the at least one processor, computing the calibration parameter based on statistical adjustment computation measures applying the detected signal discrepancy.

18. A computer readable non-transitory medium having instructions stored thereon which, when carried out on a computer, cause the computer to perform the steps of the method as claimed in claim 16.

19. The method as claimed in claim 16, further including:
   with at least one light source, directing light to the subject at a distance, the light source generating visible light and infrared light.

20. A pulse oximetry device for extracting physiological information, comprising:
   at least one light source configured to direct light radiation to the subject from a distance, the light source configured to generate light radiation spectra portions comprising visible radiation and infrared radiation;
   a photoplethysmography (PPG) camera configured to detect the visible radiation and the infrared radiation from the at least one light source reflected by the subject at a distance from the subject;
   a computer with one or more computer processors programmed to:
   receive a data stream derived from the detected visible and infrared radiation, the data stream comprising a characteristic signal including physiological information indicative of at least one vital parameter, the characteristic signal comprising at least two indicative signal components representative of detected spectral portions indicative of the at least one vital parameter, the data stream at least sectionally comprising at least one auxiliary signal component, the at least one auxiliary signal component being representative of a distinct spectral portion;
   detect a characteristic signal discrepancy between at least one of the at least two indicative signal components and the at least one auxiliary signal component related to posture of the subject,
   determine an adaptive signal calibration parameter based on the detected signal discrepancy; and
   determine the at least one vital parameter based on the at least two indicative signal components and the adaptive calibration parameter.

* * * * *